US008663098B2

(12) United States Patent
Shimada et al.

(10) Patent No.: US 8,663,098 B2
(45) Date of Patent: Mar. 4, 2014

(54) SCANNING ENDOSCOPE APPARATUS (71) Applicant: Olympus Medical Systems Corp., Tokyo (JP)

(72) Inventors: Tomoko Shimada, Hachioji (JP); Masahiro Yoshino, Machida (JP); Daiki Ariyoshi, Hachioji (JP); Makoto Igarashi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/708,220

(22) Filed: Dec. 7, 2012

(65) Prior Publication Data

US 2013/0178706 A1    Jul. 11, 2013

Related U.S. Application Data (63) Continuation of application No. PCT/JP2012/057967, filed on Mar. 27, 2012.

(30) Foreign Application Priority Data

Mar. 31, 2011    (JP) .................................. 2011-080251

(51) Int. Cl.
 *A61B 1/06*    (2006.01)
(52) U.S. Cl.
 USPC ............................ 600/181; 600/178; 600/182
(58) Field of Classification Search
 CPC ........... A61B 1/00172; A61B 1/00186; A61B 1/063; A61B 1/0638; A61B 1/0646
 See application file for complete search history.

(56) References Cited

U.S. PATENT DOCUMENTS 5,198,875 A * 3/1993 Bazin et al. .................... 356/369
5,491,329 A * 2/1996 Urakami et al. .............. 250/205
(Continued)

FOREIGN PATENT DOCUMENTS

JP    2003-535659 A    12/2003
JP    2007-526014 A    9/2007
(Continued)

OTHER PUBLICATIONS

English Abstract of International Publication No. WO 01/97902 A2, dated Dec. 27, 2001 (corresponding to JP 2003-535659 A).

(Continued)

*Primary Examiner* — Anhtuan T Nguyen
*Assistant Examiner* — Jae Woo
(74) *Attorney, Agent, or Firm* — Scully, Scott, Murphy & Presser, P.C.

(57) ABSTRACT

A scanning endoscope apparatus includes: a light source; first and second polarization sections; third and fourth polarization sections; a first wavelength separation section; a second wavelength separation section; a first detection section; and a second detection section. The scanning endoscope apparatus further includes: a first judgment section comparing light intensities of at least two of the light having a first wavelength band transmitted through the first wavelength separation section, the light having a second wavelength band transmitted through the first wavelength separation section, the light having the first wavelength band transmitted through the second wavelength separation section and the light having the second wavelength band transmitted through the second wavelength separation section to observe the return light on a surface area; and a second judgment section comparing light intensities of two which are not used by the first judgment section to observe the return light in a deep-part area of the subject.

7 Claims, 9 Drawing Sheets

(56) References Cited

U.S. PATENT DOCUMENTS

| | | | |
|---|---|---|---|
| 5,649,897 A * | 7/1997 | Nakamura et al. | 600/111 |
| 5,716,324 A * | 2/1998 | Toida | 600/160 |
| 6,063,093 A * | 5/2000 | Winston et al. | 606/108 |
| 6,177,984 B1 * | 1/2001 | Jacques | 356/39 |
| 6,470,124 B1 * | 10/2002 | Le Gargasson et al. | 385/117 |
| 6,503,195 B1 * | 1/2003 | Keller et al. | 600/160 |
| 6,530,882 B1 * | 3/2003 | Farkas et al. | 600/168 |
| 6,772,003 B2 * | 8/2004 | Kaneko et al. | 600/476 |
| 7,242,833 B2 * | 7/2007 | Yang et al. | 385/117 |
| 7,347,817 B2 * | 3/2008 | Glukhovsky et al. | 600/181 |
| 7,970,458 B2 * | 6/2011 | Norris et al. | 600/478 |
| 8,235,887 B2 * | 8/2012 | Bayer et al. | 600/113 |
| 8,556,806 B2 * | 10/2013 | Farr | 600/160 |
| 2002/0054290 A1 * | 5/2002 | Vurens et al. | 356/369 |
| 2002/0183622 A1 * | 12/2002 | Zuluaga et al. | 600/476 |
| 2004/0111031 A1 * | 6/2004 | Alfano et al. | 600/476 |
| 2005/0020926 A1 | 1/2005 | Wiklof et al. | |
| 2005/0182295 A1 * | 8/2005 | Soper et al. | 600/117 |
| 2006/0195014 A1 | 8/2006 | Seibel et al. | |
| 2007/0129601 A1 * | 6/2007 | Johnston et al. | 600/109 |
| 2007/0299309 A1 * | 12/2007 | Seibel et al. | 600/117 |
| 2008/0027286 A1 * | 1/2008 | Xie | 600/181 |
| 2009/0028407 A1 | 1/2009 | Seibel et al. | |
| 2010/0102211 A1 | 4/2010 | Murooka et al. | |
| 2011/0301418 A1 * | 12/2011 | Gharib et al. | 600/181 |
| 2012/0122053 A1 * | 5/2012 | Hackel et al. | 433/29 |
| 2013/0178706 A1 * | 7/2013 | Shimada et al. | 600/178 |
| 2013/0231536 A1 * | 9/2013 | Pascal, Amit | 600/178 |

FOREIGN PATENT DOCUMENTS

| | | |
|---|---|---|
| JP | 2008-531193 | 8/2008 |
| JP | 2009-516568 | 4/2009 |
| JP | 2009-213649 | 9/2009 |
| JP | 2010-104422 | 5/2010 |
| JP | 2010-520778 A | 6/2010 |
| JP | 2011-504782 A | 2/2011 |
| WO | WO 2005/00110 A2 | 1/2005 |
| WO | WO 2006/093655 A2 | 9/2006 |
| WO | WO 2007/067163 A1 | 6/2007 |
| WO | WO 2008/111970 A1 | 9/2008 |
| WO | WO 2009/070160 A1 | 6/2009 |

OTHER PUBLICATIONS

International Search Report dated May 1, 2012 issued in PCT/JP2012/057967.

* cited by examiner

INSIDE OF CAP

FIG.12

INSIDE OF CAP

SCANNING ENDOSCOPE APPARATUS

CROSS REFERENCE TO RELATED APPLICATION

This application is a continuation application of PCT/JP2012/057967 filed on Mar. 27, 2012 and claims benefit of Japanese Application No. 2011-080251 filed in Japan on Mar. 31, 2011, the entire contents of which are incorporated herein by this reference.

BACKGROUND OF THE INVENTION

1. Field of the Invention

The present invention relates to a scanning endoscope apparatus.

2. Description of the Related Art

Conventionally, a scanning endoscope apparatus has been proposed which causes a distal end of an optical fiber guiding unpolarized light from a light source to perform scanning and receives return light from a subject with an optical fiber bundle arranged around the optical fiber to generate an image using a light intensity signal sequentially detected over time (see, for example, Japanese Patent Application Laid-Open Publication No. 2003-535659).

Furthermore, an endoscope apparatus is proposed which is for, at the time of performing observation and the like using an endoscope, observing a polarized image using polarization, for example, for diagnosis of early-stage cancer and the like, in addition to observation using unpolarized light (see, for example, Japanese Patent Application Laid-Open Publication No. 2009-213649, and Japanese Patent Application Laid-Open Publication No. 2010-104422).

In the endoscope apparatus of Japanese Patent Application Laid-Open Publication No. 2009-213649, by providing a polarization separation device and an image pickup device such as a CCD, at a distal end portion of an endoscope distal end, a polarization component of return light of light illuminating a living body can be separated.

The endoscope apparatus of Japanese Patent Application Laid-Open Publication No. 2010-104422 sequentially radiates multiple illumination lights in different polarization states to an observation site for each different wavelength spectrum by sequentially switching among respective multiple color filters and multiple illumination light polarization filters. Then, after polarizing return light from the observation site with a polarization filter section provided at a distal end portion of an endoscope in a predetermined direction, the endoscope apparatus performs image pickup with an image pickup device such as a CCD.

SUMMARY OF THE INVENTION

A scanning endoscope apparatus of an aspect of the present invention is a scanning endoscope apparatus for scanning illumination light to generate an endoscopic image of a subject, the scanning endoscope apparatus including: a light source emitting first illumination light of a first wavelength band and second illumination light of a second wavelength band different from the first wavelength band; a first polarization section transmitting light in a first polarization direction of the first illumination light, which is to be radiated to the subject; a second polarization section transmitting light in a second polarization direction of the second illumination light, which is to be radiated to the subject, the second polarization direction being different from the first polarization direction; a third polarization section receiving return light from the subject and transmitting the light in the first polarization direction; a fourth polarization section receiving the return light from the subject and transmitting the light in the second polarization direction; a first wavelength separation section separating the light transmitted through the third polarization section into light of the first wavelength band and light of the second wavelength band; a second wavelength separation section separating the light transmitted through the fourth polarization section into the light of the first wavelength band and the light of the second wavelength band; a first detection section detecting light intensities of the light having the first wavelength band transmitted through the first wavelength separation section and the light having the second wavelength band transmitted through the first wavelength separation section; a second detection section detecting light intensities of the light having the first wavelength band transmitted through the second wavelength separation section and the light having the second wavelength band transmitted through the second wavelength separation section; a first judgment section comparing the light intensities of at least two of the light having the first wavelength band transmitted through the first wavelength separation section, the light having the second wavelength band transmitted through the first wavelength separation section, the light having the first wavelength band transmitted through the second wavelength separation section and the light having the second wavelength band transmitted through the second wavelength separation section in order to observe the return light on a surface area of the subject; and a second judgment section comparing the light intensities of two of the light having the first wavelength band transmitted through the first wavelength separation section, the light having the second wavelength band transmitted through the first wavelength separation section, the light having the first wavelength band transmitted through the second wavelength separation section and the light having the second wavelength band transmitted through the second wavelength separation section in order to observe the return light in a deep-part area of the subject, the two lights not being used by the first judgment section.

DETAILED DESCRIPTION OF THE PREFERRED EMBODIMENTS

Embodiments of the present invention will be described below with reference to drawings.
(First Embodiment)

A first embodiment will be described below.

First, a configuration of an endoscope apparatus of the first embodiment will be described with the use of FIGS. 1 to 3.

Figure 1:
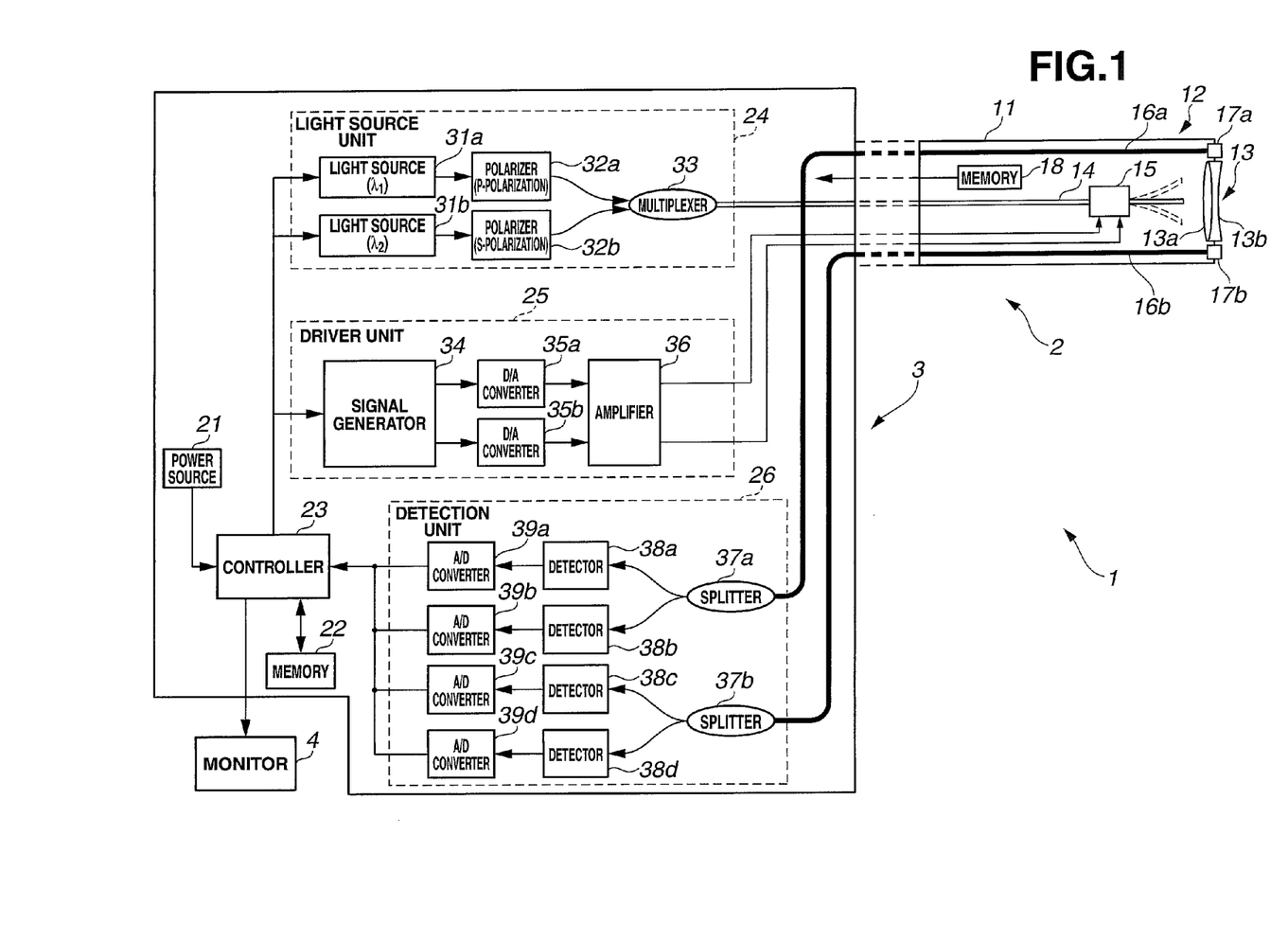
FIG. 1 is a diagram showing a configuration of an endoscope apparatus according to a first embodiment.
Figure 2:
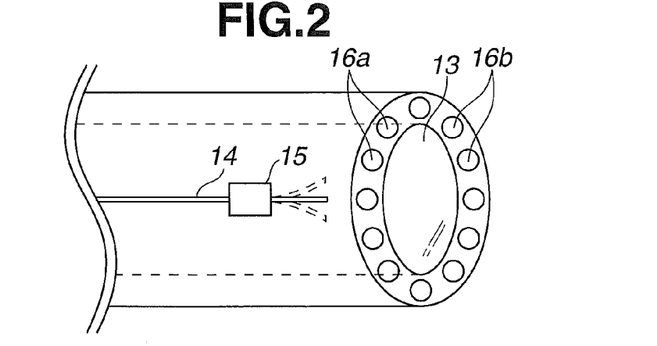
FIG. 2 is a perspective view showing a configuration of a distal end portion of the endoscope apparatus.

FIG. 1 is a diagram showing the configuration of the endoscope apparatus according to the first embodiment; FIG. 2 is a perspective view showing a configuration of a distal end portion of the endoscope apparatus; and FIG. 3 is a diagram for illustrating arrangement of polarization filters on the distal end portion.

As shown in FIG. 1, an endoscope apparatus 1 is configured to have a scanning endoscope 2 which radiates illumination light to a subject while scanning the illumination light, and obtains return light from the subject, a body apparatus 3 connected to the endoscope 2, and a monitor 4 which displays a subject image obtained by the body apparatus 3.

The endoscope 2 has an elongated insertion portion 11 configured mainly with a tube body having predetermined flexibility. On the distal end side of the insertion portion 11, a distal end portion 12 is provided. On the proximal end side of the insertion portion 11, a connector and the like not shown are provided. The endoscope 2 is configured being detachably connectable to the body apparatus 3 via the connector and the like.

On the distal end face of the distal end portion 12, a distal end optical system 13 configured with illumination lenses 13a and 13b is provided. Inside the insertion portion 11, an illumination fiber 14 as an optical device, which is inserted from the proximal end side to the distal end side to guide light from a light source unit 24 to be described later, and an actuator 15 provided on the distal end side of the illumination fiber 14 to cause the distal end of the illumination fiber 14 to perform scanning in a desired direction on the basis of a driving signal from a driver unit 25 to be described later are provided. By such a configuration, illumination light from the light source unit 24 guided by the illumination fiber 14 is radiated to the subject.

Inside the insertion portion 11, a detection fiber 16a inserted from the proximal end side to the distal end side along the internal circumference of the insertion portion 11 to guide a first polarization component as a light reception section which receives return light from the subject and a detection fiber 16b which guides a second polarization component are provided. Each of the detection fibers 16a and 16b may be a fiber bundle constituted by at least two or more fibers. When the endoscope 2 is connected to the body apparatus 3, the detection fibers 16a and 16b are connected to splitters 37a and 37b to be described later.

Figure 3:
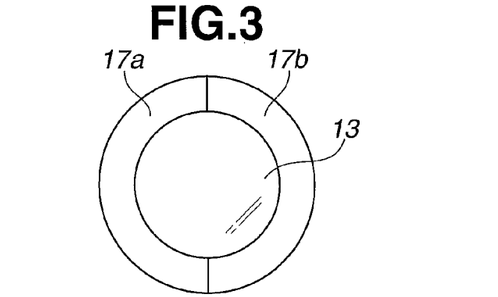
FIG. 3 is a diagram for illustrating arrangement of polarization filters on the distal end portion.

As shown in FIG. 3, on the distal end face of the distal end portion 12, a polarization filter 17a which transmits return light in a first polarization direction from the subject and a polarization filter 17b which transmits return light in a second polarization direction from the subject are symmetrically provided around the distal end optical system 13. As shown in FIG. 1, the polarization filters 17a and 17b are provided such that the polarization filters 17a and 17b cover the distal ends of the detection fibers 16a and 16b. The polarization filter 17a as a first polarization filter and the polarization filter 17b as a second polarization filter are provided between the subject and the detection fibers 16a and 16b, respectively, to polarize return light from the subject in a desired direction. Note that, in FIG. 1, the polarization filters 17a and 17b are arranged on the upper side and the lower side, respectively, for convenience. Arrangement of the polarization filters 17a and 17b on the distal end portion 12 is not limited to FIG. 3.

Figure 4A:
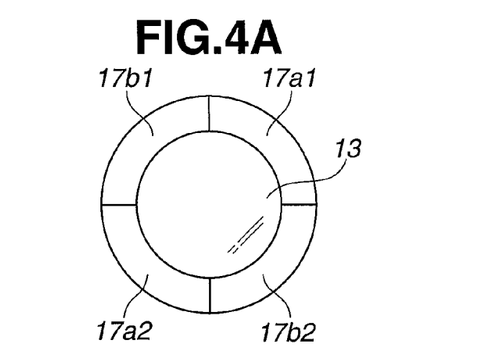
FIG. 4A is a diagram for illustrating another example of arrangement of polarization filters on the distal end portion.
Figure 4B:
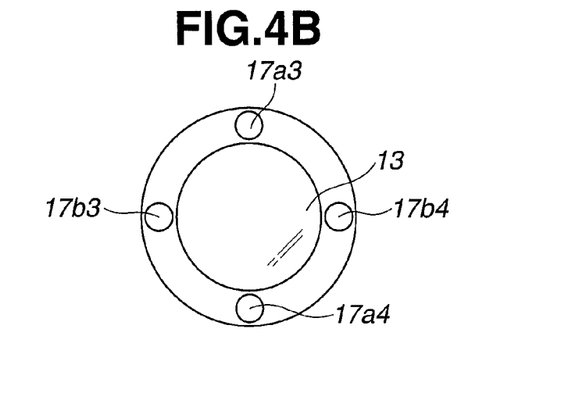
FIG. 4B is a diagram for illustrating another example of arrangement of polarization filters on the distal end portion.
Figure 4C:
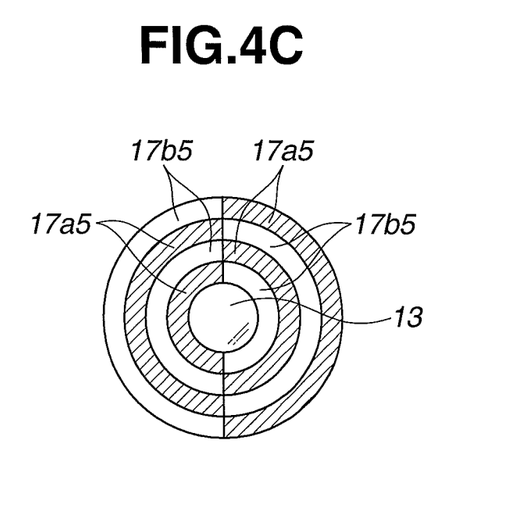
FIG. 4C is a diagram for illustrating another example of arrangement of polarization filters on the distal end portion.

FIGS. 4A to 4C are diagrams for illustrating other examples of arrangement of the polarization filters on the distal end portion.

On the distal end face in FIG. 4A, polarization filters 17a1 and 17a2 for the first polarization direction and polarization filters 17b1 and 17b2 for the second polarization direction are arranged in circular symmetry. Due to such arrangement, it is possible to suppress lack of balance of detected quantity of light of each polarization component dependent on arrangement of the detection fibers 16a and 16b on the distal end.

On the distal end face in FIG. 4B, polarization filters 17a3 and 17a4 for the first polarization direction are arranged vertically relative to the surface of the sheet and polarization filters 17b3 and 17b4 for the second polarization direction are arranged horizontally relative to the surface of the sheet. By arranging the polarization filters 17a3, 17a4, 17b3 and 17b4 at equal intervals in circular symmetry as described above, return light from the subject may be received by the detection fibers 16a and 16b without polarizing the return light, at positions around the distal end optical system 13 where the polarization filters 17a3, 17a4, 17b3 and 17b4 are not arranged.

On the distal end face in FIG. 4C, two areas are defined by a line segment passing through the center of the distal end face of the endoscope 2. Each of the two areas is divided into multiple areas, four areas here, from the center toward the circumference, and polarization filters 17a5 and 17b5 with different polarization characteristics are alternately provided for the multiple areas, with a line segment passing through the center of the distal end face of the endoscope 2 as a border. Due to such arrangement, it is possible to suppress lack of balance of detected quantity of light in the horizontal direction and in the direction from the center toward the circumference, similarly to FIG. 4A.

Returning to FIG. 1, a memory 18 storing various information about the endoscope 2 is provided inside the insertion portion 11. When the endoscope 2 is connected to the body apparatus 3, the memory 18 is connected to a controller 23 to be described later via a signal line not shown, and the various information about the endoscope 2 is read by the controller 23.

The body apparatus 3 is configured to have a power source 21, a memory 22, the controller 23, the light source unit 24, the driver unit 25 and a detection unit 26.

The light source unit 24 is configured to have two light sources 31a and 31b, two polarizers 32a and 32b, and a multiplexer 33.

The driver unit 25 is configured to have a signal generator 34, digital-analog (hereinafter referred to as D/A) converters 35a and 35b, and an amplifier 36.

The detection unit 26 is configured to have the splitters 37a and 37b, detectors 38a to 38d, and analog-digital (hereinafter referred to as A/D) converters 39a to 39d.

The power source 21 controls supply of a power source to the controller 23 according to an operation of a power source switch or the like not shown. The memory 22 stores a control program and the like for controlling the whole body apparatus 3.

When a power source is supplied from the power source 21, the controller 23 reads the control program from the memory 22 to control the light source unit 24 and the driver unit 25, and analyzes the light intensity of return light from the subject detected by the detection unit 26 to perform control to display an obtained subject image on the monitor 4.

The light sources 31a and 31b of the light source unit 24 adjust polarization directions of lights of different wavelength bands with the use of the polarizers 32a and 32b, respectively, on the basis of control by the controller 23. More specifically, the light source 31a emits light $\lambda_1$ of a first wavelength band of 390 nm to 445 nm or 530 nm to 550 nm to the polarizer 32a, and the light source 31b emits light $\lambda_2$ of a second wavelength band of 600 nm to 1100 nm to the polarizer 32b. Especially, it is desirable that the light $\lambda_1$ of the first wavelength band is 415 nm and the light $\lambda_2$ of the second wavelength band is 600 nm.

The polarizers 32a and 32b have different polarization characteristics, respectively, and polarize the lights $\lambda_1$ and $\lambda_2$ emitted from the light sources 31a and 31b. More specifically, the polarizer 32a polarizes the light $\lambda_1$ of the first wavelength band from the light source 31a in a first polarization direction (P polarization). The polarizer 32b polarizes the light $\lambda_2$ of the second wavelength band from the light source 31b in a second polarization direction (S polarization) which is different from the first polarization direction. Here, the lights $\lambda_1$ and $\lambda_2$ polarized by the polarizers 32a and 32b are referred to as lights $\lambda_{1P}$ and $\lambda_{2S}$, respectively. The first wavelength band having the first polarization direction has a light absorption characteristic of the subject, and the second wavelength band having the second polarization direction has a light absorption characteristic lower than the light absorption characteristic of the first wavelength band.

The multiplexer 33 multiplexes the light $\lambda_{1P}$ of the first wavelength band polarized into the first polarization direction and the light $\lambda_{2S}$ of the second wavelength band polarized into the second polarization direction. Thereby, the lights $\lambda_{1P}$ and $\lambda_{2S}$ having the different polarization characteristics are emitted from the light source unit 24 to the illumination fiber 14 through the two wavelength bands.

Thus, the light source unit 24 constitutes a light source section which emits lights having different polarization characteristics through at least two wavelength bands.

The signal generator 34 of the driver unit 25 outputs a driving signal for causing the distal end of the illumination fiber 14 to perform scanning in a desired direction, for example, in a spiral shape, on the basis of control by the controller 23. More specifically, the signal generator 34 outputs a driving signal for driving the distal end of the illumination fiber 14 in a horizontal direction (X-axis direction) relative to an insertion axis of the insertion portion 11, to the D/A converter 35a, and outputs a driving signal for driving the distal end of the illumination fiber 14 in a vertical direction (Y-axis direction) relative to the insertion axis of the insertion portion 11, to the D/A converter 35b.

The D/A converters 35a and 35b convert the respective inputted driving signals from digital signals to analog signals, and output the analog signals to the amplifier 36. The amplifier 36 amplifies the inputted driving signals and outputs the signals to the actuator 15. The actuator 15 causes the distal end of the illumination fiber 14 to perform scanning in a spiral shape, on the basis of the driving signals from the amplifier 36. Thereby, the lights $\lambda_{1P}$ and $\lambda_{2S}$ emitted from the light source unit 24 to the illumination fiber 14 are sequentially radiated to the subject in a spiral shape.

Thus, the driver unit 25 constitutes a driving section which causes an end of the illumination fiber 14 to perform scanning.

From the light $\lambda_{1P}$ radiated to the subject, return light $\lambda_{1P}$ reflected from a surface-part area of the subject, the polarization characteristic of which has not changed, and return light $\lambda_{1S}$ reflected from a deep-part area of the subject, the polarization characteristic of which has changed, are obtained. Similarly, from the light $\lambda_{2S}$ radiated to the subject, return light $\lambda_{2S}$ reflected from the surface-part area of the subject, the polarization characteristic of which has not changed, and return light $\lambda_{2P}$ reflected from the deep-part area of the subject, the polarization characteristic of which has changed, are obtained. The polarization filter 17a transmits the return lights $\lambda_{1P}$ and $\lambda_{2P}$, and the polarization filter 17b transmits the return lights $\lambda_{1S}$ and $\lambda_{2S}$. The return lights $\lambda_{1P}$ and $\lambda_{2P}$ and the return lights $\lambda_{1S}$ and $\lambda_{2S}$ are received by the detection fibers 16a and 16b, respectively. The return lights $\lambda_{1P}$ and $\lambda_{2P}$ received by the detection fiber 16a are guided to the splitter 37a, and the return lights $\lambda_{1S}$ and $\lambda_{2S}$ received by the detection fiber 16b are guided to the splitter 37b.

The splitters 37a and 37b are, for example, dichroic mirrors or the like, and the splitters 37a and 37b split return light in a predetermined wavelength band. More specifically, the splitter 37a splits the return lights $\lambda_{1P}$ and $\lambda_{2P}$ guided by the detection fiber 16a into return light $\lambda_{1P}$ of the first wavelength band and return light $\lambda_{2P}$ of the second wavelength band and outputs the return lights $\lambda_{1P}$ and $\lambda_{2P}$ to the detectors 38a and 38b, respectively. Similarly, the splitter 37b splits the return lights $\lambda_{1S}$ and $\lambda_{2S}$ guided by the detection fiber 16b into return light $\lambda_{1S}$ of the first wavelength band and return light $\lambda_{2S}$ of the second wavelength band and outputs the return lights $\lambda_{1S}$ and $\lambda_{2S}$ to the detectors 38c and 38d, respectively.

The detector 38a detects the light intensity of the return light $\lambda_{1P}$ of the first wavelength band in the first polarization direction, and the detector 38b detects the light intensity of the return light $\lambda_{2P}$ of the second wavelength band in the first polarization direction. Similarly, the detector 38c detects the light intensity of the return light $\lambda_{1S}$ of the first wavelength band in the second polarization direction, and the detector 38d detects the light intensity of the return light $\lambda_{2S}$ of the second wavelength band in the second polarization direction. Signals of the light intensities detected by the detectors 38a to 38d are outputted to the A/D converters 39a to 39d, respectively. Thus, the detectors 38a to 38d constitute a detection section which detects the light intensities of return lights from a subject.

The A/D converters 39a to 39d convert the signals of the light intensities outputted from the detectors 38a to 38d, respectively, from analog signals to digital signals and output the digital signals to the controller 23.

The controller 23 performs comparison between the light intensity in the first polarization direction and the light intensity in the second polarization direction on the surface-part area of the subject and comparison between the light intensity in the first polarization direction and the light intensity in the second polarization direction in the deep-part area of the subject. The comparisons between the light intensities is performed, for example, by performing division or subtraction between the light intensity in the first polarization direction and the light intensity in the second polarization direction on the surface-part area of the subject. Thus, the controller 23 constitutes a calculation section which performs division or subtraction between the light intensity in the first polarization direction and the light intensity in the second polarization direction.

More specifically, the controller 23 performs comparison between the light intensity of the return light $\lambda_{1P}$ detected by the detector 38a and the light intensity of the return light $\lambda_{2S}$ detected by the detector 38d, and comparison between the light intensity of the return light $\lambda_{2P}$ detected by the detector 38b and the light intensity of the return light $\lambda_{1S}$ detected by the detector 38c. By performing comparison of the light intensities for the respective wavelengths on the surface-part area and comparison of the light intensities for the respective wavelengths in the deep-part area, the controller 23 generates pseudo-color images for different depths of the subject and displays the images on the monitor 4. Furthermore, the controller 23 judges whether or not there is a lesion, such as a tumor, on the surface-part area and in the deep-part area by detecting whether or not the compared light intensities are lower than a predetermined threshold.

Next, operation of the endoscope apparatus 1 configured as described above will be described with the use of FIG. 5.

Figure 5:
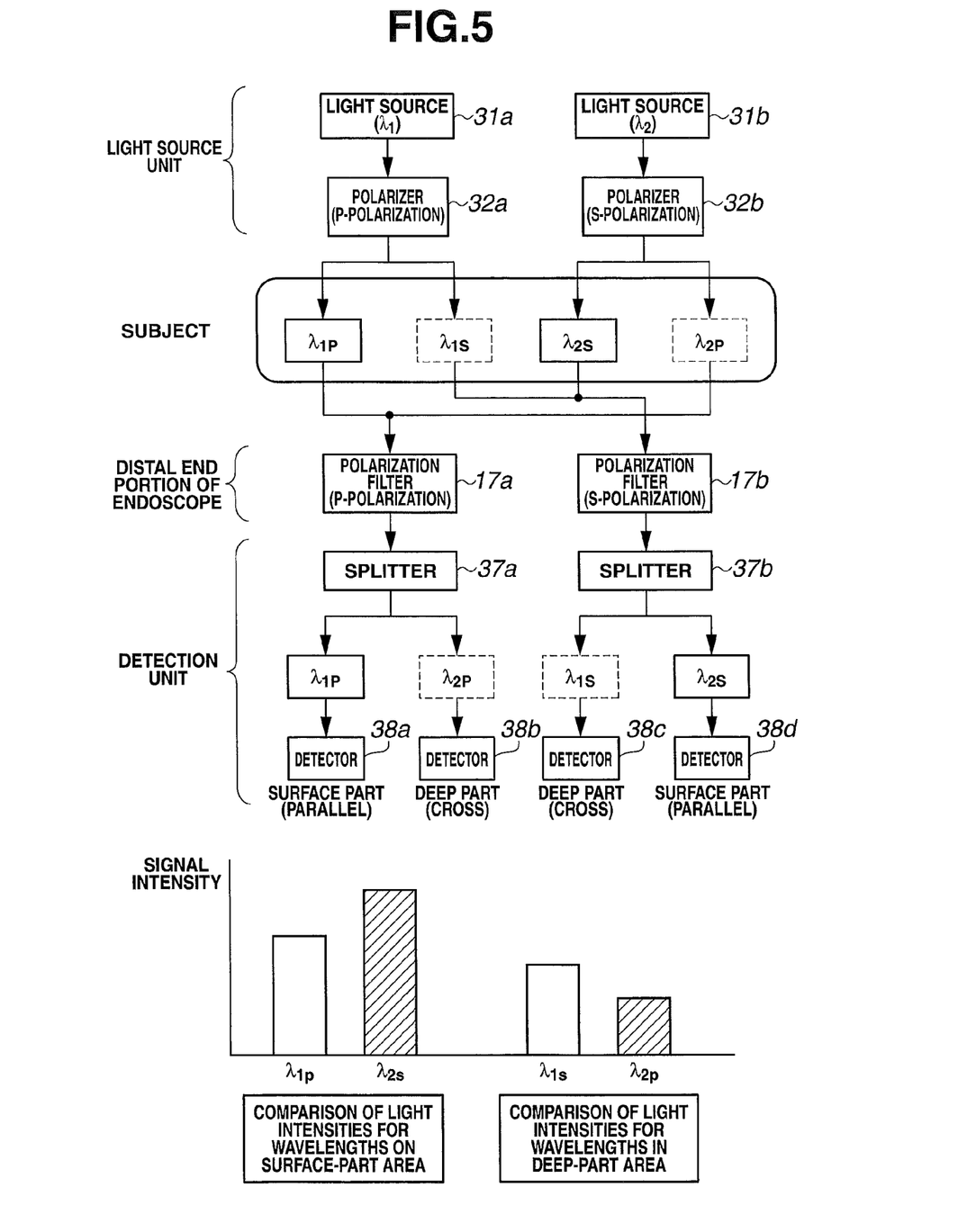
FIG. 5 is a diagram for illustrating operation of an endoscope apparatus 1.

FIG. 5 is a diagram for illustrating operation of the endoscope apparatus 1.

First, when the power source switch is turned on by an operator, and a power source from the power source 21 is supplied to the controller 23, light $\lambda_1$ of the first wavelength band and light $\lambda_2$ of the second wavelength band are outputted from the light sources 31a and 31b, respectively. The light $\lambda_1$ of the first wavelength band outputted from the light source 31a is polarized into the first polarization direction by the polarizer 32a, and the light $\lambda_2$ of the second wavelength band outputted from the light source 31b is polarized into the second polarization direction by the polarizer 32b. Light $\lambda_{1P}$ of the first wavelength band which has been polarized into the first polarization direction and light $\lambda_{2S}$ of the second wavelength band which has been polarized into the second polarization direction are emitted from the illumination fiber 14 and radiated to the subject. Return lights $\lambda_{1P}$ and $\lambda_{2S}$ reflected on a surface part and return lights $\lambda_{1S}$ and $\lambda_{2P}$ reflected in a deep part are obtained from the subject.

The return lights $\lambda_{1P}$, $\lambda_{2S}$, $\lambda_{1S}$ and $\lambda_{2P}$ are separated into the return lights $\lambda_{1P}$ and $\lambda_{2P}$ in the first polarization direction by the polarization filters 17a, and the return lights $\lambda_{1S}$ and $\lambda_{2S}$ in the second polarization direction by the polarization filter 17b. The return lights $\lambda_{1P}$ and $\lambda_{2P}$ separated by the polarization filter 17a are split at a predetermined wavelength band by the splitter 37a, and return lights $\lambda_{1S}$ and $\lambda_{2S}$ separated by the polarization filter 17b are split at a predetermined wavelength band by the splitter 37b.

The light intensities of the return lights $\lambda_{1P}$ and $\lambda_{2P}$ split by the splitter 37a are detected by the detectors 38a and 38b, respectively, and the light intensities of the return lights $\lambda_{1S}$ and $\lambda_{2S}$ split by the splitter 37b are detected by the detectors 38c and 38d, respectively. Comparison of the detected light intensities for the respective wavelengths on the surface-part area and comparison of the detected light intensities for the respective wavelengths in the deep part are performed by the controller 23 to judge existence or nonexistence of a tumor or the like on the surface-part area and in the deep part.

Next, a method for analyzing polarized image diagnosis using the endoscope apparatus 1 will be described.

Figure 6:
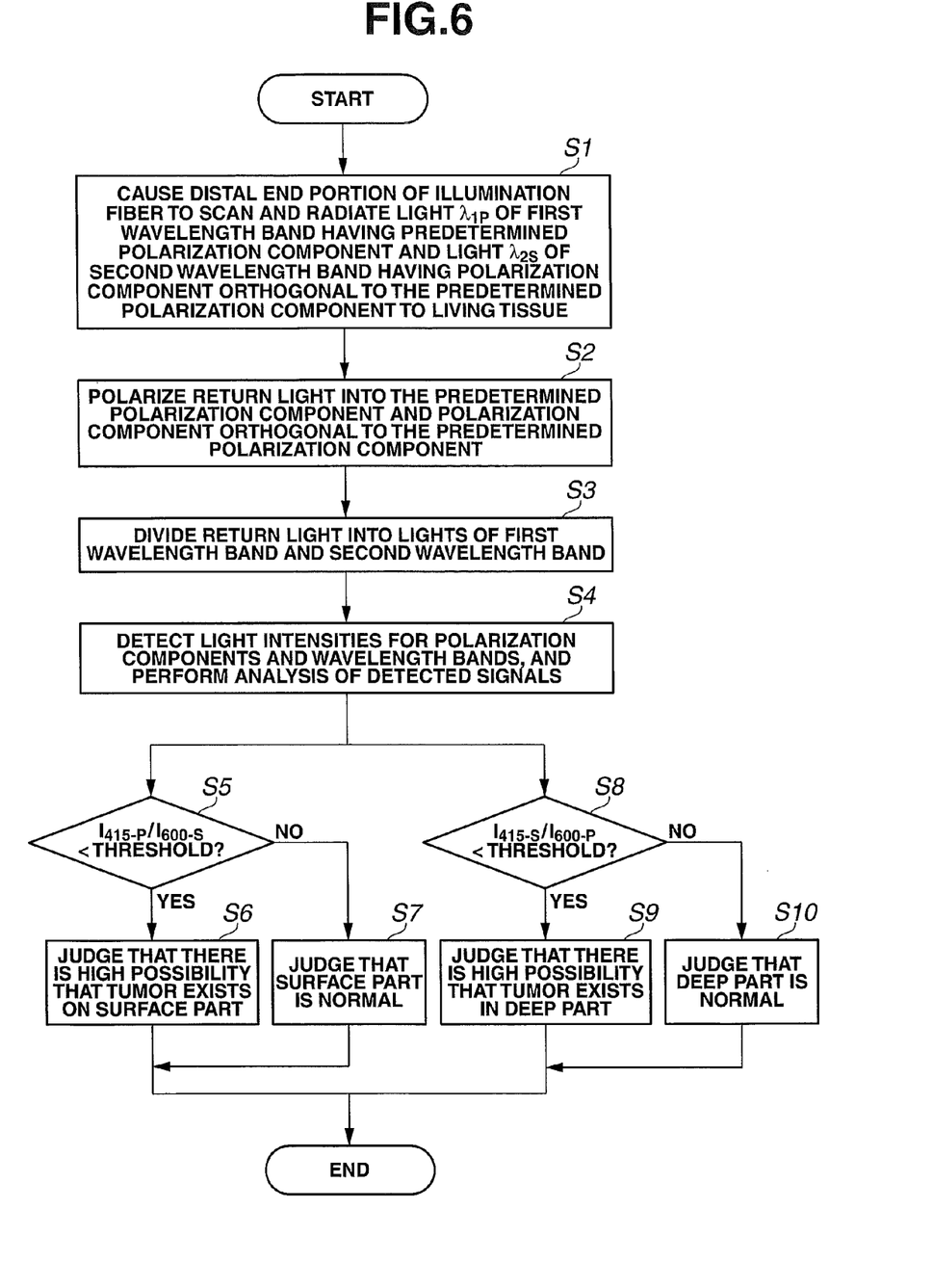
FIG. 6 is a flowchart for illustrating an example of a process flow of polarized image diagnosis using the endoscope apparatus 1.

FIG. 6 is a flowchart for illustrating an example of a process flow of the polarized image diagnosis using the endoscope apparatus 1.

First, the distal end portion of the illumination fiber 14 is caused to perform scanning, and light $\lambda_{1P}$ of the first wavelength band having a predetermined polarization component and light $\lambda_{2S}$ of the second wavelength band having a polarization component orthogonal to the predetermined polarization component are radiated to living tissue (step S1). Next, return light is polarized into the predetermined polarization component and the polarization component orthogonal to the predetermined polarization component (step S2). Here, the center wavelength of the first wavelength band is assumed to be 415 nm, and the center wavelength of the second wavelength band is assumed to be 600 nm. Next, the return lights are divided into lights of the first wavelength band and the second wavelength band (step S3). The light intensities for the polarization components and the wavelength bands are detected, and analysis of detected signals is performed (step S4).

Next, it is judged whether or not a result of division between light intensity $I_{415-P}$ of the return light of the first wavelength band from the surface part of the subject and light intensity $I_{600-S}$ of the return light of the second wavelength band from the surface part of the subject is smaller than a threshold (step S5). If it is judged that the result of the light intensity $I_{415-P}$/the light intensity $I_{600-S}$ of the return light from the surface part is smaller than the threshold, the judgment result is YES, and it is judged that there is a high possibility that a lot of hemoglobin having a 415-nm absorption characteristic exist on the surface part (step S6). On the other hand, if it is judged that the result of the light intensity $I_{415-P}$/the light intensity $I_{600-S}$ of the return light from the surface part is equal to or above the threshold, the judgment result is NO, and it is judged that the surface part is normal (step S7).

Furthermore, it is judged whether or not a result of division between light intensity $I_{415-S}$ of the return light of the first wavelength band from the deep part of the subject and light intensity $I_{600-P}$ of the return light of the second wavelength band from the deep part of the subject is smaller than a threshold (step S8). The process of step S8 is executed in parallel with the process of step S5. If it is judged that the result of the light intensity $I_{415-S}$/the light intensity $I_{600-P}$ of the return light from the deep part is smaller than the threshold, the judgment result is YES, and it is judged that there is a high possibility that a lot of hemoglobin exist in the deep part (step S9). On the other hand, if it is judged that the result of the light intensity $I_{415-S}$/the light intensity $I_{600-P}$ of the return light from the deep part is equal to or above the threshold, the judgment result is NO, and it is judged that the deep part is normal (step S10). Then, when existence or nonexistence of a tumor on the surface part of the subject and in the deep part thereof is judged, the process ends.

Next, treatment using the endoscope apparatus 1 performed when a tumor or the like is detected by the method for analyzing polarized image diagnosis will be described.

Figure 7:
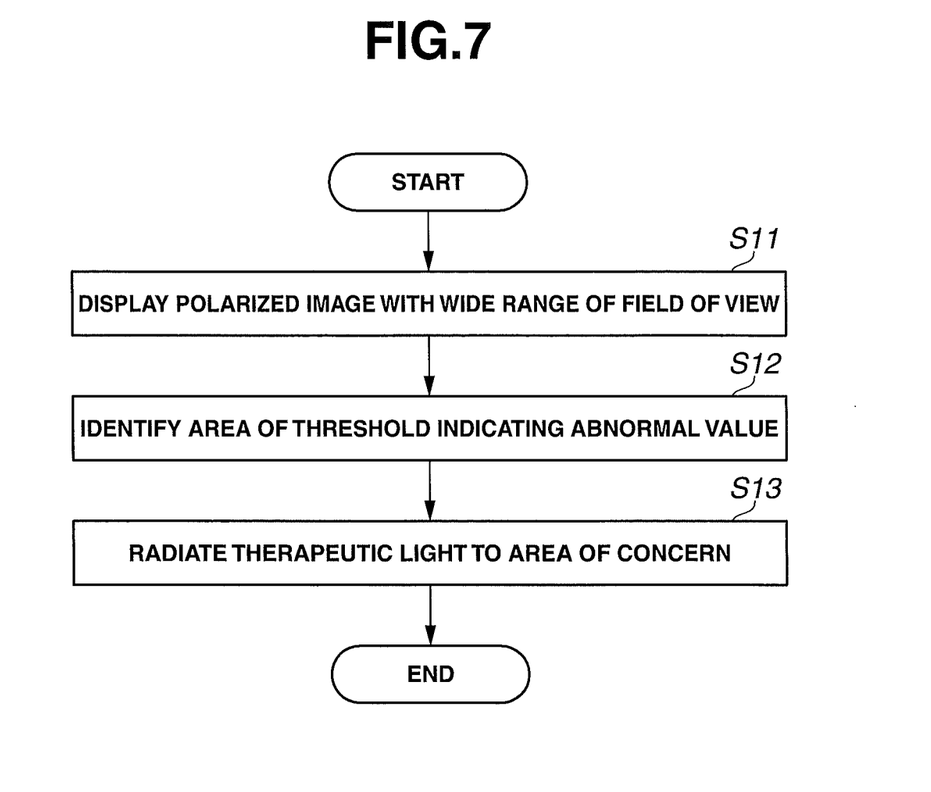
FIG. 7 is a flowchart for illustrating an example of a flow of treatment using the endoscope apparatus 1.

FIG. 7 is a flowchart for illustrating an example of a flow of the treatment using the endoscope apparatus 1.

First, a polarized image with a wide range of field of view is displayed on the monitor 4 (step S11). Next, an area of threshold indicating an abnormal value is identified (step S12). Lastly, therapeutic light is radiated to the identified area of concern (step S13), and the process ends.

As described above, the endoscope apparatus 1 scans the light $\lambda_{1P}$ of the first wavelength band having the first polarization direction (polarization characteristic) and the light $\lambda_{2S}$ of the second wavelength band having the second polarization direction (polarization characteristic) to a subject, and polarizes return lights from the subject with the polarization filters 17a and 17b on the distal end portion 12. Then, the endoscope apparatus 1 separates the return lights polarized by the polarization filters 17a and 17b at a predetermined wavelength band, detects light intensities and obtains a polarized image. As a result, it becomes unnecessary to provide an image pickup device, such as a CCD, for the distal end portion 12, and it is possible to obtain a polarized image with a high image quality while the small diameter of the insertion portion 11 is maintained.

Thus, according to the endoscope apparatus of the present embodiment, it is possible to obtain an image with a high image quality while the small diameter of the insertion portion is maintained.

(Modifications)

In the case of a common fiber, there may be a case where, even if polarized light enters, the polarization state cannot be retained in light emitted from the fiber due to influence of change in the structure of the fiber caused by bending or the like of an insertion portion. Therefore, in the present modifications, description will be made on endoscope apparatuses capable of, even if a fiber structure changes due to bending or the like of an insertion portion, retaining a polarization state.

Figure 8:
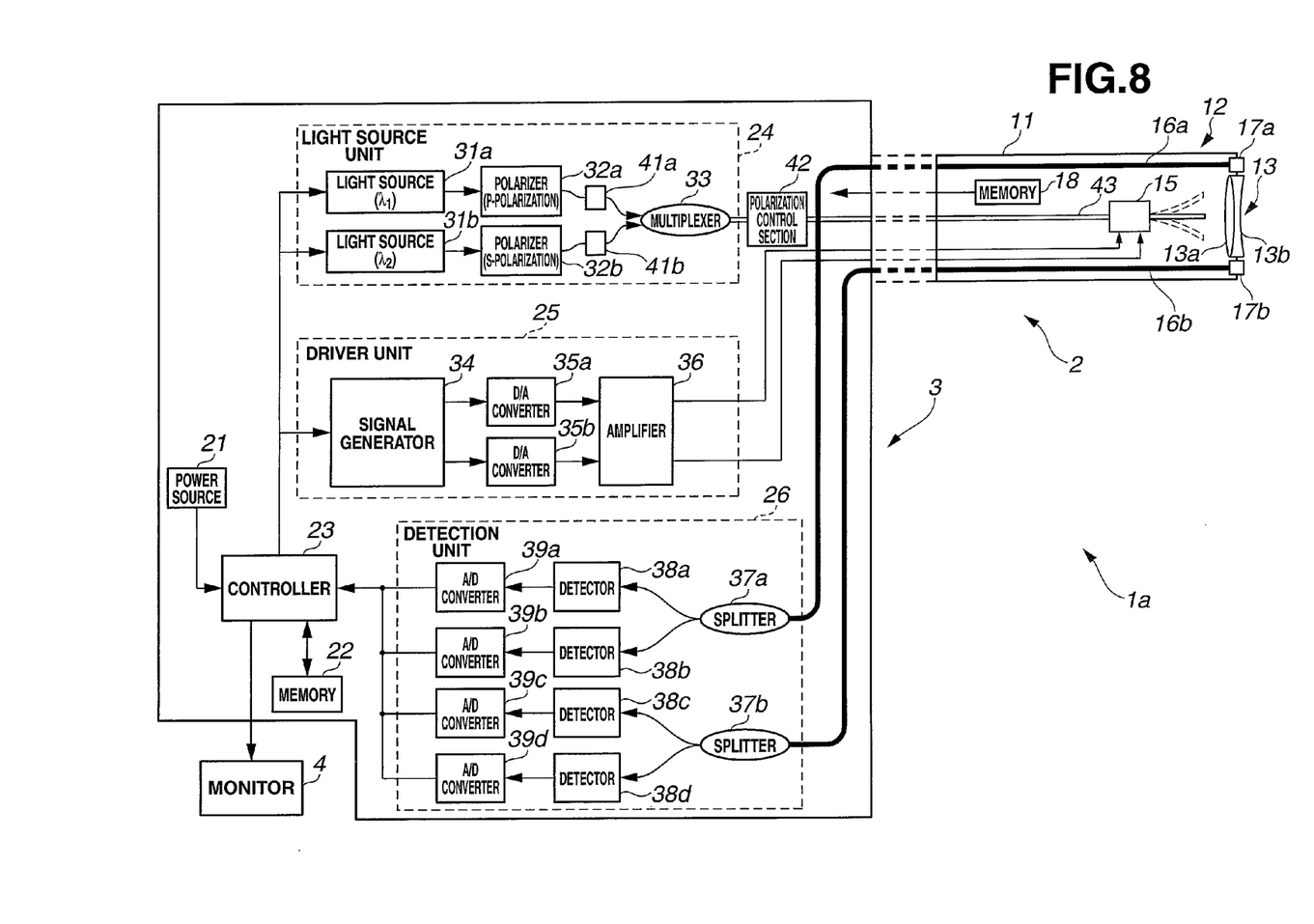
FIG. 8 is a diagram showing a configuration of an endoscope apparatus according to a first modification of the first embodiment.

FIG. 8 is a diagram showing a configuration of an endoscope apparatus according to a first modification of the first embodiment.

As shown in FIG. 8, in an endoscope apparatus 1a of the present modification, phase compensation sections 41a and 41b are provided at output stages of the polarizers 32a and 32b of the endoscope apparatus 1 in FIG. 1, and a polarization control section 42 is provided at an output stage of the multiplexer 33. The endoscope apparatus 1a of the present modification is configured with a single-mode fiber 43 instead of the illumination fiber 14 in FIG. 1.

The phase compensation section 41a performs phase compensation of the light $\lambda_{1P}$ of the first wavelength band in the first polarization direction emitted from the polarizer 32a and emits the light $\lambda_{1P}$ to the multiplexer 33. The phase compensation section 41b performs phase compensation of the light $\lambda_{2S}$ of the second wavelength band in the second polarization direction emitted from the polarizer 32b and emits the light $\lambda_{2S}$ to the multiplexer 33.

The polarization control section 42 adjusts the polarization direction of illumination light from the multiplexer 33 and emits the illumination light to the single-mode fiber 43. The single-mode fiber 43 emits the illumination light from the polarization control section 42 from the distal end face and radiates the illumination light to a subject via the distal end optical system 13. Since other components are similar to those of the endoscope apparatus 1 of the first embodiment, description thereof are omitted.

Due to such a configuration, the endoscope apparatus 1a can retain the polarization state of illumination light even if the fiber structure changes due to bending or the like of the insertion portion 11.

Figure 9:
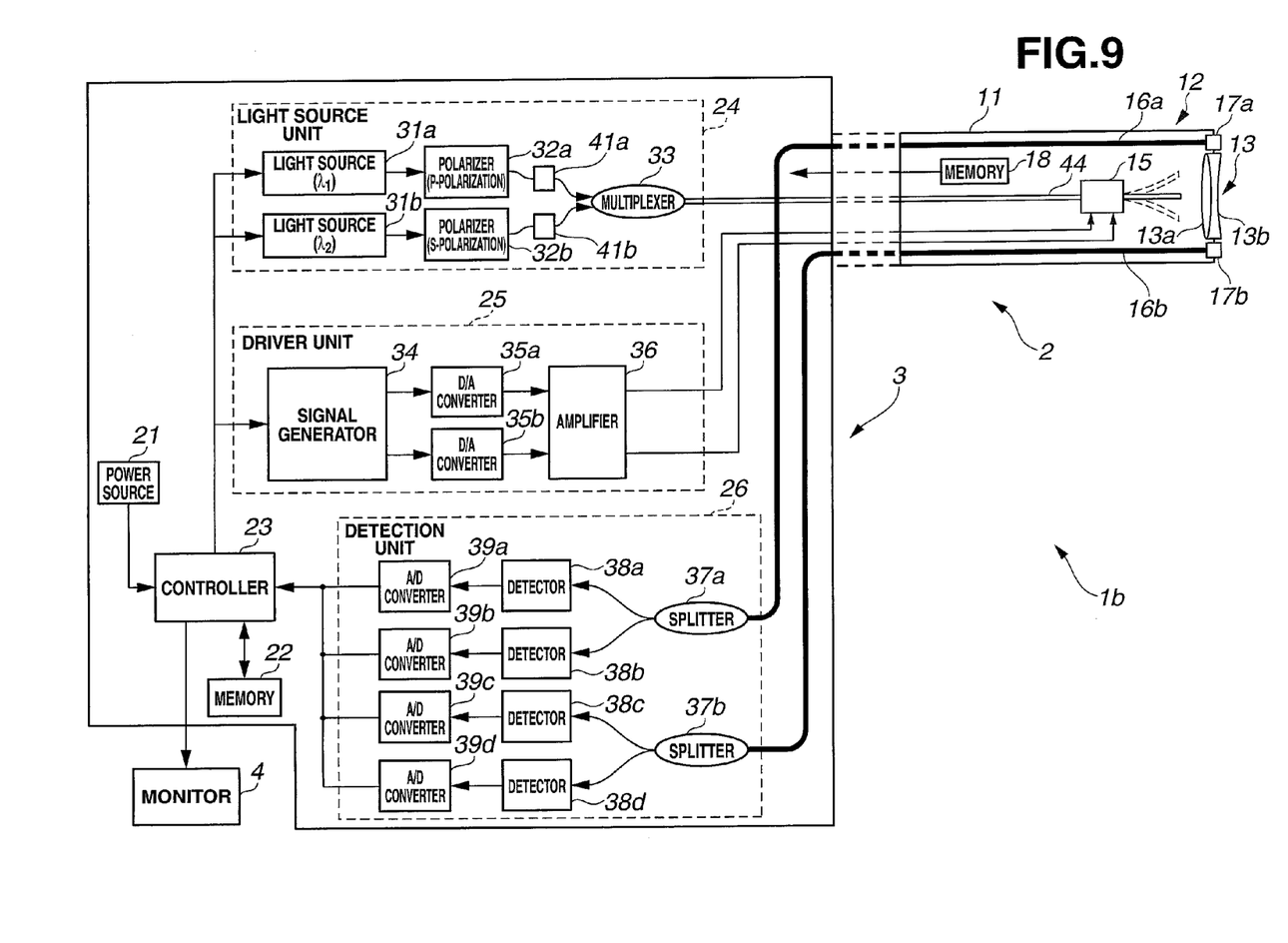
FIG. 9 is a diagram showing a configuration of an endoscope apparatus according to a second modification of the first embodiment.

FIG. 9 is a diagram showing a configuration of an endoscope apparatus according to a second modification of the first embodiment.

As shown in FIG. 9, an endoscope apparatus 1b is configured such that the polarization control section 42 of the endoscope apparatus 1a of the first modification is eliminated and a polarization retention fiber 44 is used instead of the single-mode fiber 43.

The polarization retention fiber 44 is such a fiber that polarizations of input and output correspond to each other. The polarization retention fiber 44 retains polarization of illumination light inputted from the multiplexer 33 and radiates the illumination light to a subject from the distal end face. Since other components are similar to those of the endoscope apparatus 1a of the first modification, description thereof are omitted. Furthermore, polarization retention fibers may be used for the detection fibers 16a and 16b.

Due to such a configuration, the endoscope apparatus 1b can retain the polarization state of illumination light even if the fiber structure changes due to bending or the like of the insertion portion 11, similarly to the endoscope apparatus 1a of the first modification.

(Second Embodiment)

Next, a second embodiment will be described.

Figure 10:
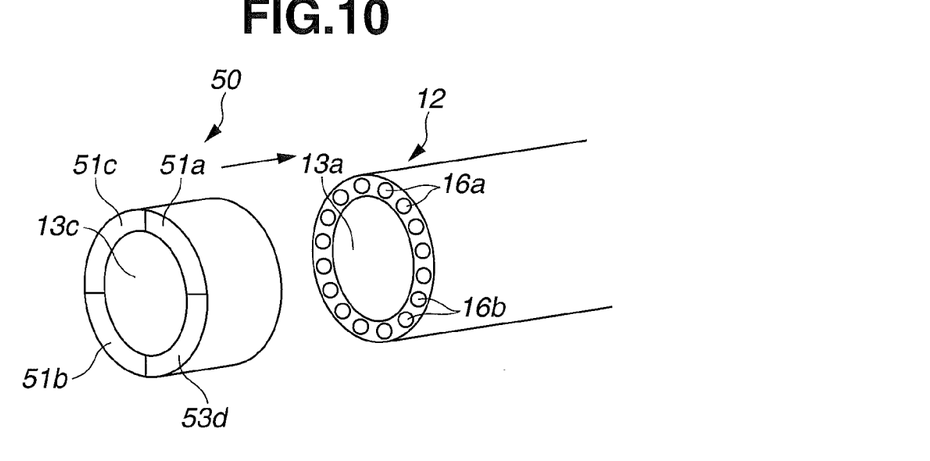
FIG. 10 is a perspective view showing a distal end configuration of an endoscope apparatus of a second embodiment.
Figure 11:
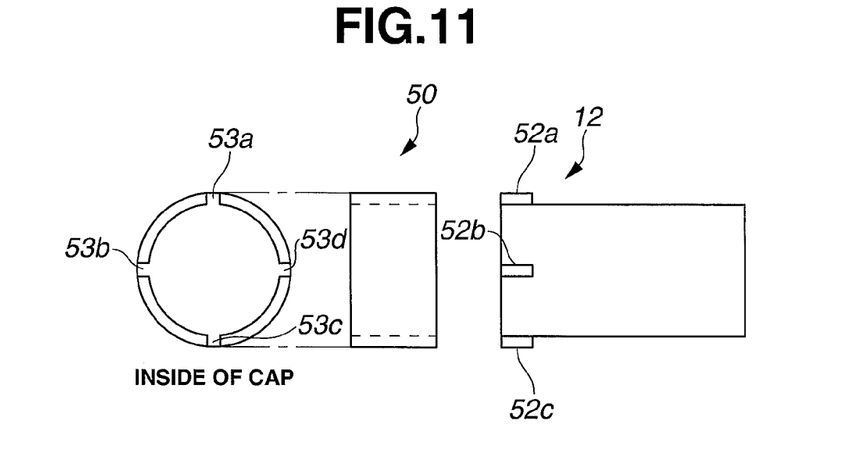
FIG. 11 is a side view showing the distal end configuration of the second embodiment and a diagram showing a configuration of an inner surface of a cap.
Figure 12:
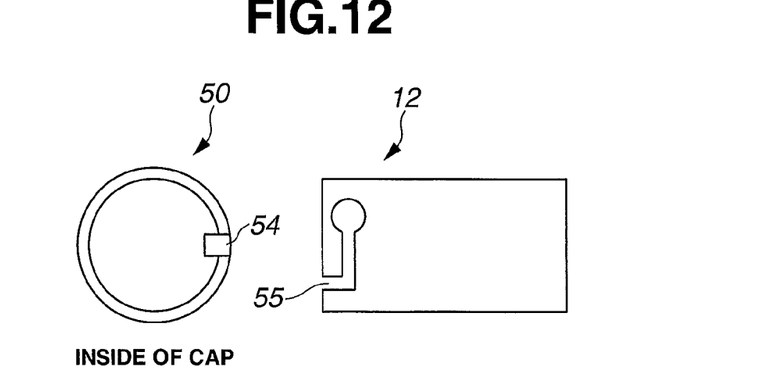
FIG. 12 is a diagram showing another distal end configuration of the endoscope apparatus.

FIG. 10 is a perspective view showing a distal end configuration of an endoscope apparatus of the second embodiment; FIG. 11 is a side view showing the distal end configuration of the second embodiment and a diagram showing a configuration of an inner surface of a cap; and FIG. 12 is a diagram showing another distal end configuration of the endoscope apparatus. Note that the same components as those of the endoscope apparatus 1 of the first embodiment will be given the same reference numerals, and description thereof are omitted.

An endoscope apparatus 1c of the present embodiment is configured to have an endoscope 2a and a cap 50 in a cylindrical shape which is attachable to and detachable from the distal end portion 12 of the endoscope 2a, in addition to the body apparatus 3 and the monitor 4 of the first embodiment.

An illumination lens 13a is provided on the distal end face of the distal end portion 12, and the detection fiber 16a guiding a first polarization component and the detection fiber 16b guiding a second polarization component are arranged around the illumination lens 13a.

The cap 50 as an endoscope cap may be provided with an illumination lens cover 13c, such as a flat lens, for covering the illumination lens 13a. The illumination lens cover 13c constitutes an optical member which transmits light radiated from the illumination fiber 14 to a subject.

The cap 50 is provided with polarization filters 51a and 51b for P-polarization and polarization filters 51c and 51d for S-polarization covering the detection fibers 16a and 16b. The polarization filters 51a and 51b and the polarization filters 51c and 51d for S-polarization are arranged in circular symmetry. The polarization filters 51a to 51d constitute a polarization filter section which separates return light from the subject according to polarization characteristics. In the present embodiment, arrangement of the polarization filters 51a to 51d is similar to the arrangement in FIG. 4A described above. Note that the arrangement of the polarization filters 51a to 51d may be the arrangement in FIG. 3, FIG. 4B or FIG. 4C described above.

Four protruding portions 52a to 52d are provided on the outer circumferential face of the distal end portion 12. Note that, in FIG. 11, since the protruding portion 52d is arranged on the back side of the protruding portion 52b, the reference numeral of the protruding portion 52d is omitted. Four groove portions 53a to 53d into which the four protruding portions 52a to 52d can be fitted, respectively, are provided on the inner surface of the cap 50. The groove portions 53a to 53d constitute a fitting section for attachment to and detachment from the endoscope 2. The groove portions 53a to 53d constitute a concavo-convex portion for preventing the cap 50 from rotating relative to the endoscope 2. The cap 50 is fitted to the distal end portion 12 in a state that the protruding portions 52a to 52d are fitted with the groove portions 53a to 53d.

Note that, though description has been made on the assumption of the configuration in which the distal end portion 12 is provided with the protruding portions 52a to 52d, and the cap 50 is provided with the groove portions 53a to 53d, for example, such a configuration is also possible that the distal end portion is provided with the groove portions, and the cap 50 is provided with the protruding portions. Each of the number of the protruding portions 52a to 52d and the number of the groove portions 53a to 53d is not limited to four and may be three or fewer or five or more. Furthermore, the cap 50 and the distal end portion 12 may be fixed with screws or the like.

Furthermore, as shown in FIG. 12, a protruding portion 54 constituting a cam may be provided on the inner surface of the cap 50, and the distal end portion 12 may be provided with a cam groove 55. An operator fixes the cap 50 and the distal end portion 12 by rotating the cap 50 after fitting the protruding portion 54 into the cam groove 55. The protruding portion 54 constitutes a rotation prevention section which prevents rotation of the cap 50 relative to the endoscope 2.

In order to further prevent the cap from coming off while preventing rotation of the cap, flexible elastic material having elasticity, for example, silicon, urethane or the like may be used for the material of a part of the cap 50 covering the endoscope 2.

According to such a configuration, when desiring to obtain a polarized image having a polarization characteristic different from that of the cap 50, the operator can easily obtain the polarized image having a different polarization characteristic only by fitting a cap provided with a polarization filter having the polarization characteristic different from that of the cap 50 to the distal end portion 12.

Thus, according to the endoscope apparatus 1c of the present embodiment, it is possible to easily obtain a polarized image having a different polarization characteristic.

Note that, as for the respective steps in each flowchart in the present specification, it is also possible to change the execution order, execute multiple steps at the same time, or execute the steps in different order for each execution as long as such change is not inconsistent with the nature of the steps.

The present invention is not limited to the embodiments and modifications described above, and various modifications, alterations and the like are possible within a range not departing from the spirit of the present invention.

What is claimed is:

1. A scanning endoscope apparatus for scanning illumination light to generate an endoscopic image of a subject, the scanning endoscope apparatus comprising:
   a light source emitting first illumination light of a first wavelength band and second illumination light of a second wavelength band different from the first wavelength band;
   a first polarization section transmitting light in a first polarization direction of the first illumination light, which is to be radiated to the subject;
   a second polarization section transmitting light in a second polarization direction of the second illumination light, which is to be radiated to the subject, the second polarization direction being different from the first polarization direction;
   a third polarization section receiving return light from the subject and transmitting the light in the first polarization direction;
   a fourth polarization section receiving the return light from the subject and transmitting the light in the second polarization direction;
   a first wavelength separation section separating the light transmitted through the third polarization section into light of the first wavelength band and light of the second wavelength band;
   a second wavelength separation section separating the light transmitted through the fourth polarization section into the light of the first wavelength band and the light of the second wavelength band;
   a first detection section detecting light intensities of the light having the first wavelength band transmitted through the first wavelength separation section and the light having the second wavelength band transmitted through the first wavelength separation section;
   a second detection section detecting light intensities of the light having the first wavelength band transmitted through the second wavelength separation section and the light having the second wavelength band transmitted through the second wavelength separation section;
   a first judgment section comparing the light intensities of at least two of the light having the first wavelength band transmitted through the first wavelength separation section, the light having the second wavelength band transmitted through the first wavelength separation section, the light having the first wavelength band transmitted through the second wavelength separation section and the light having the second wavelength band transmitted through the second wavelength separation section in order to observe the return light on a surface area of the subject; and
   a second judgment section comparing the light intensities of two of the light having the first wavelength band transmitted through the first wavelength separation section, the light having the second wavelength band transmitted through the first wavelength separation section, the light having the first wavelength band transmitted through the second wavelength separation section and the light having the second wavelength band transmitted through the second wavelength separation section in order to observe the return light in a deep-part area of the subject, the two lights not being used by the first judgment section.

2. The scanning endoscope apparatus according to claim 1, wherein the first wavelength band is from 390 nm to 445 nm.

3. The scanning endoscope apparatus according to claim 2, wherein the first wavelength band includes at least 415 nm.

4. The scanning endoscope apparatus according to claim 1, wherein the second wavelength band is from 600 nm to 1100 nm.

5. The scanning endoscope apparatus according to claim 4, wherein the second wavelength band includes at least 600 nm.

6. The scanning endoscope apparatus according to claim 1, wherein the first judgment section uses the light intensity of the light having the first wavelength band transmitted through the first wavelength separation section.

7. The scanning endoscope apparatus according to claim 6, wherein the first judgment section compares the light intensity of the light having the first wavelength band transmitted through the first wavelength separation section with the light intensity of the light having the second wavelength band transmitted through the second wavelength separation section, and the second judgment section compares the light intensity of the light having the second wavelength band transmitted through the first wavelength separation section with the light intensity of the light having the first wavelength band transmitted through the second wavelength separation section.

* * * * *